United States Patent

Michaud et al.

[11] Patent Number: 6,143,324
[45] Date of Patent: Nov. 7, 2000

[54] FREE-FLOWABLE DIRECTLY COMPRESSIBLE STARCH AS BINDER, DISINTEGRANT AND FILLER FOR COMPRESSION TABLETS AND HARD GELATINE CAPSULES

[75] Inventors: Jacques Marie Loic Michaud, Brussels; Dirk Reimond Provoost, Vilvoorde; Elsie Van Bogaert, Bornem, all of Belgium

[73] Assignee: Cerestar Holdings B.V., LA Sas van Gent, Netherlands

[21] Appl. No.: 09/112,984

[22] Filed: Jul. 10, 1998

[30] Foreign Application Priority Data

Feb. 3, 1998 [GB] United Kingdom .................. 9802201

[51] Int. Cl.$^7$ .............................. A61K 9/14; A61K 9/20; A61K 9/48
[52] U.S. Cl. .................. 424/465; 424/452; 424/489; 424/464; 514/778; 514/951; 514/960
[58] Field of Search ...................................... 424/451, 456, 424/464, 465, 489, 452

[56] References Cited

U.S. PATENT DOCUMENTS

| | | | |
|---|---|---|---|
| 3,034,911 | 5/1962 | McKee et al. | 106/210 |
| 3,490,742 | 1/1970 | Nichols et al. | 252/99 |
| 3,622,677 | 11/1971 | Short et al. | 424/361 |
| 3,956,515 | 5/1976 | Moore et al. | 426/302 |
| 4,072,535 | 2/1978 | Short et al. | 106/210 |
| 4,369,308 | 1/1983 | Trubiano | 536/106 |
| 4,383,111 | 5/1983 | Takeo et al. | 536/102 |
| 4,384,005 | 5/1983 | McSweeney | 426/250 |
| 4,551,177 | 11/1985 | Trubiano et al. | 106/210 |
| 5,164,014 | 11/1992 | Brancq et al. | 127/32 |
| 5,560,927 | 10/1996 | Menon et al. | 424/464 |

FOREIGN PATENT DOCUMENTS

| | | |
|---|---|---|
| 0 130 683 | 1/1985 | European Pat. Off. . |
| 402186A2 | 12/1990 | European Pat. Off. . |
| 1216873 | 12/1970 | United Kingdom . |

OTHER PUBLICATIONS

Gelatinazation of Starch During Cooking of Spaghetti, Marshall, et al. Cereal Chemistry, pp. 146,–147, 1974.

*Primary Examiner*—James M. Spear
*Attorney, Agent, or Firm*—Pillsbury Madison & Sutro LLP

[57] ABSTRACT

A directly compressible starch consisting in an intense white free-flowing powder showing both excellent compression profile and extremely good disintegration properties. This starch is especially designed to be used as a binder in direct compression processes where it yields very hard white tablets at relatively low compression forces. Tablets resulting from the compression of the above mentioned starch disintegrate in an aqueous medium at a very high speed and they additionally exhibit low friability pattern. This free-flowing starch also brings advantages when used as filler and binder in the filling of some hard gelatine capsules especially for these which are filled by pre-compression of the ingredients. This starch is characterized by regular and smooth partially swollen granules which can be either birefringent or non-birefringent. It can be prepared by spray-drying of a partially cooked starch.

19 Claims, 3 Drawing Sheets

FREE-FLOWABLE DIRECTLY COMPRESSIBLE STARCH AS BINDER, DISINTEGRANT AND FILLER FOR COMPRESSION TABLETS AND HARD GELATINE CAPSULES

This invention relates to a free-flowing compressible processed starch powder suitable for use both as a binder and as a disintegrant in tablets or capsules and to a process for producing this.

Tablets and capsules are amongst the most frequently employed delivery forms for most medicinal preparations. This situation can be explained by the fact that these dosage forms allow a good accuracy of dosage of the active component of the medicinal formulation. Furthermore, as no liquids are generally involved in the process for preparing these medicinal formulations, handling and packaging are a lot easier. Last but not least, conservation and stability of these preparations are generally better than those of other formulations.

The same arguments also explain the reason why tablets are often used as media for other applications such as food, including confectionery products, aromas or sweeteners, detergents, dyes or phytosanitary products.

Tablets can be manufactured using three main processes, wet granulation, dry granulation and direct compression.

In wet granulation, components are typically mixed and granulated using a wet binder, the wet granulates are then sieved, dried and eventually ground prior to compressing the tablets.

In dry granulation, powdered components are typically mixed prior to being compacted, also called pre-compression, to yield hard slugs which are then ground and sieved before the addition of other ingredients and final compression.

Direct compression is now considered to be the simplest and the most economical process for producing tablets. This process requires only two steps; i.e., the mixing of all the ingredients and the compression of this mixture.

Hard gelatine capsules are usually filled with their ingredients according to two possible techniques. One uses gravity when these ingredients are poured into the capsule due to their natural flow. The other involves partial compression according to which the ingredients are compressed inside a calibrated punch prior to being deposited into the capsule.

A component of a tablet or capsule is usually defined as being either an excipient or an active ingredient. Active ingredients are normally ones that trigger a pharmaceutical, chemical or nutritive effect and they are present only up to the strict limit necessary for providing this effect in the right proportion. Excipients are chemically and pharmaceutically inert ingredients which are included to facilitate the preparation of the dosage forms or to adapt the release of the active ingredients.

Excipients, when intended for direct compression, must fulfil a certain number of properties. They should have a high flowability. They should have a high compressibility, a good pressure-hardness profile. They should be compatible with all types of active ingredients and not interfere with their biological availability, they also should be stable against ageing, air moisture and heat. They should be colourless and tasteless. And finally they should possess proper mouthfeel.

Excipients can be characterised according to their function during the formulation as, for instance, binders, disintegrants, fillers (or diluents), glidants, lubricants and eventually flavours, sweeteners and dyes.

Lubricants are intended to improve the ejection of the compressed tablet from the die of the tablet-making equipment or from the punches used for compressing ingredients for introduction into capsules.

Glidants are added to improve the powder flow. They are typically used to help the mixture of all the components to fill evenly and regularly the die before the compression.

Fillers are inert ingredients sometimes used as bulking agents in order to decrease the concentration of the active ingredient in the final formulation. The function of filler may, in some cases, be also provided by the binder.

Disintegrants may be added to formulations in order to help the tablets disintegrate when they are placed in a liquid environment and so release the active ingredient. The disintegration properties are, mostly, based upon the ability of the disintegrant to swell in the presence of a fluid, such as water or gastric juice. This swelling disrupts the continuity of the tablet structure and thus, allows the different components to enter into solution or into suspension. Commonly used disintegrants include native starches, modified starches, modified celluloses, microcrystalline cellulose or alginates.

Binders are used to hold together the structure of the dosage forms. They have the property to bind together all the other ingredients after sufficient compression forces have been applied and they provide the integrity of the tablets. Commonly used compression binders include pregelatinised starches, polyvinylpyrrolidone, methylcellulose, microcrystalline cellulose, sucrose, lactose, dextrose, sorbitol or mannitol.

Starches are known to act in some cases as binders and in some other cases as disintegrants according to the fact that they are native, chemically modified or physically modified.

Native granular starches and, to a smaller extent, cooked starches (also referred to as pregelatinised starches) can show somewhat limited binding capacities when employed in direct compression. Cooked starches, even when they are satisfactory as binders are not satisfactory in terms of disintegration. These starches do not really disperse, they show the tendency to prevent the penetration of water into the tablet, thus preventing its disintegration, by forming a tacky film on its surface.

EP-A-0402186 describes a directly compressible starch mixture obtained by mixing 1 to 20% of a starch paste with 99–80% of native starch. The starch paste is obtained by treating native starch at 85° C. which results in breaking of the starch granules.

Partially cold water swellable starches for use as binders and/or disintegrants in the manufacture of tablets by direct compression and as fillers for formulations supplied in hard gelatine capsules, are described in U.S. Pat. No. 3,622,677 and U.S. Pat. No. 4,072,535. The material described is essentially a pre-compacted starch powder obtained by subjecting a non-gelatinised granular starch to physical compaction between steel rollers with the possible input of thermal energy. The compacted starch shows the presence of sharp birefringent granules and non-birefringent granules as well as some aggregates of granules and fragments dried to a moisture content of 9–16%. After the compactation the starch is ground and sieved to yield a free flowing powder. The above mentioned starch powders exhibit limited binding capacity in direct compression and poor disintegration properties.

Other cold water swellable physically modified starches are described as being useful as disintegrant but with very poor binding properties (see U.S. Pat. No. 4,383,111). In that case, the granular starch is cooked in the presence of water and possibly an organic solvent at temperature not higher than 10° C. higher than its gelatinisation temperature. The so-obtained starch is then dried resulting in non-birefringent granules.

Chemical modification of starch has also been investigated. Crosslinked pregelatinised starches such as starch phosphates, starch adipates, starch sulphates, starch glycolates or carboxymethyl starches are useful as disintegrants although they exhibit poor binding capacities (see U.S. Pat. No. 3,034,911 and U.S. Pat. No. 4,369,308).

Acid and enzyme hydrolysed starches are reported to be useful as binders (U.S. Pat. No. 4,551,177). These compressible starches are prepared by treating a granular starch with an acid and/or alpha-amylase enzyme at a temperature below the gelatinisation temperature of the starch. These treated starches show altered and weakened granules with disrupted surfaces. These starches are said to be useful as binders for tabletting as well as binders and fillers for capsule filling and are said to exhibit reasonable disintegration properties.

Dextrinised starches (see U.S. Pat. No. 4,384,005) and starch fractions such as non-granular amylose (see U.S. Pat. No. 3,490,742) are also described as having limited binding and/or disintegration properties. These are of limited interest due to the expensive processes needed for their preparation.

It appears clearly that there is a need for a free-flowing directly compressible starch powder showing both an excellent compression profile and very good disintegration properties and which is neither chemically modified nor chemically or enzymatically treated and without the use of an organic solvent.

According to the present invention there is provided a free-flowing directly compressible processed starch powder characterised in that it comprises regular and smooth partially swollen granules of starch wherein the ratio of non-swollen birefringent granules to swollen non-birefringent granules is in the range of from 1:5 to 5:1 and in that it has an average particle size greater than 50 μm and a moisture content of from 3 to 15% by weight. The processed starch powder according to the invention is suitable for use as a binder in direct compression processes yielding very hard tablets at relatively low compression forces as well as suitable for use as a binder and/or filler in the preparation of capsule dosage forms. Tablets resulting from the compression of the above-mentioned starch disintegrate in an aqueous medium at a high speed and, additionally, exhibit a low friability pattern.

The starch powder of the invention is characterised by regular and smooth either birefringent or non-birefringent partially swollen granules. The ratio between non-swollen birefringent granules and swollen non-birefringent granules can vary from 1:5 to 5:1, preferably from 1:2 to 2:1, and is typically preferred to be around 1:1, as characterised by polarised optical microscopy. The particle size of the free-flowing direct compressible starch powder is noticeably bigger than that of the raw material starch and has an average value greater than 50 μm, typically from 50 to 500 μm (about 95 μm in the case of maize starch). Further agglomeration of granules is also possible in order to increase particle size and to adapt the flow of the powder.

According to the present invention there is provided a process for preparing a free-flowing compressible starch powder comprising the steps; 1) preparing a slurry of starch in water, 2) heating the slurry to a temperature not substantially higher than the gelatinisation temperature of the starch to cause partial swelling of the starch granules without causing disruption of the starch granules, 3) cooling the starch slurry to prevent any further swelling of the starch granules and 4) spray-drying the cooled slurry to produce a free-flowing starch powder having a moisture content of from 3 to 15% by weight.

Suitable free-flowing direct compressible starch powder can be obtained either by diluting the starch base powder in demineralised water in order to form a slurry at a concentration of from 10 and 40%, calculated on dry substance basis, or by using a starch slurry resulting from the process applied to any relevant starch containing plant (slurry of a concentration of 20% is preferred as being a good compromise between the workability of the product and the economical viability of the process).

The starch slurry is then heated at a temperature close to the gelatinisation temperature of the starch used such that starch granules start swelling without being disrupted and solubilised in the water. This temperature depends upon the plant source. For maize starch this is typically around 62° C. although starches from other sources will require different heating temperatures. We have found that a starch slurry heated to a temperature of more than 5° C. higher than the gelatinisation temperature of the starch used will result in a viscous paste that cannot be processed further in an aqueous medium according to the process of the present invention. Therefore, a relatively strict control of the temperature within a range of ±5° C. of the gelatinisation temperature of the starch used is important. Preferably, the temperature to which the starch slurry is heated is controlled to within a range of ±3° C., and more preferably within the range of ±1° C., of the gelatinisation temperature of the starch used. The temperature will depend on the type of starch used. The aim always is to obtain a starch which is partially birefringent and partially non-birefringent. The residence time in the heating device can vary from 30 sec. to 10 min. and is typically around 1 min. The heating device can be any heat exchanger, although a direct steam injection heater is preferred because it allows a better control of the temperature and the residence time. After heating the partially swollen starch slurry is cooled, typically to a temperature 5–15° C. lower than the heating temperature, in order to stabilise the product and to prevent further swelling or bursting of starch granules. Preferably a reduction of 6–7° C. in the temperature is applied. The stabilised slurry is then spray-dried using a spray-drying tower equipped either with nozzles or with turbines. Inlet and outlet temperatures are controlled such that the final free-flowing direct compressible starch powder has a moisture content of 3–15%, preferably 5–10% depending upon pharmaceutical dosage forms in the use of which this free-flowing direct compressible starch is intended.

The free-flowing direct compressible starch powder of the invention can be derived from any starch containing plant source. This includes maize (either normal maize or hybrids such as white maize, waxy maize and high-amylose containing maizes), wheat, potato, rice, sorghum, tapioca, cassava and any other similar starch-containing plants. White maize and high-amylose starches are preferred because of the better characteristics of the final products as described in the following examples.

The free-flowing direct compressible starch powder of the invention is useful as a binder and/or a disintegrant for tablets prepared by direct compression, wet granulation or dry granulation. It is also useful as a binder and a filler in the process of filling capsules.

A further embodiment of the present invention comprises a composition for the formulation of capsules and tablets prepared either by direct compression or, to a smaller extent by dry or wet granulation, containing the above-mentioned starch powders referred to as free-flowing directly compressible starch powders together with at least one active material.

Tablets obtained using the free-flowing directly compressible starch powders of the present invention as binder and disintegrant are characterised by the fact that they show very high hardness at relatively low compression forces whilst they are also capable of disintegrating in an aqueous medium at a high speed, and additionally exhibit a low friability pattern. Free-flowing directly compressible starch powders of the present invention, can be used as binder-disintegrant either alone or in conjunction, at any useful ratio, with any other binders and or disintegrants. Useful dosage of the free-flowing directly compressible starch powders of the invention varies depending upon active ingredients and other excipients and can be comprised from 2 to 95%.

A free-flowing compressible process starch powder may be characterized in that it comprises regular and smooth partially swollen granulars of starch wherein the ratio of non-swollen birefringent granules to swollen non-birefringent granules is in the range of 1:5 to 5:1 and in that it has an average particle size greater than 50 µm and a moisture content of from 3 to 15% by weight. The free-flowing compressible process starch powders according to the present invention can be compressed into tablets which exhibit a tensile strength of at least 1 N/mm² when the free-flowing compressible process starch powder is compressed into a tablet under a compression force of 10 kN.

The figures are attached to help the understanding of the nature of the treatments applied to the starch during the process.

EXAMPLE 1

This example describes the production of a free-flowing directly compressible starch powder based on a granular white maize starch hybrid. The granular white maize starch powder was diluted in demineralised water in order to form a slurry at a concentration of 20% calculated on dry substance resulting in a slurry with a relative density of 1.085 compared to water. The starch slurry was then heated in a direct steam injection heat exchanger at a temperature of 62° C. with a variation of no more than ±1° C. If the temperature reached 64° C., a viscous paste was obtained which could not be processed further. Microscopic examination of such a paste revealed the absence of birefringent granules. The heating time was maintained for a time of 1 minute. The partially swollen starch slurry was then cooled down to a temperature of 55–57° C. by cold water. Drying of the cooled partially swollen starch slurry was carried out using a Alfa-Laval spray-drying tower equipped with a turbine turning at a maximum speed of 13,000 rd/min and fed at 2.7–3.1 m³/h. The inlet temperature was fixed at 252° C. and the outlet temperature was fixed at around 81° C. in order to obtain a product with a final dry substance of around 91%. The intense white free-flowing powder obtained as described showed an average particle size of 95 µm compared to 20 µm for the initial granular white maize starch as shown in Table 1.

TABLE 1

| Starch | 1–10 µm | 10–25 µm | 25–50 µm | 50–75 µm | 75–100 µm | 100–125 µm | 125–150 µm | 150–200 µm | 200–300 µm | loose density |
|---|---|---|---|---|---|---|---|---|---|---|
| Native (%) | 12.5 | 80.1 | 6.5 | 0.7 | 0.2 | 0 | 0 | 0 | 0 | 500 g/l |
| Processed (%) | 0.3 | 8.3 | 18.2 | 16.3 | 19.4 | 10 | 12.5 | 9 | 6.0 | 510 g/l |

Figure 1:
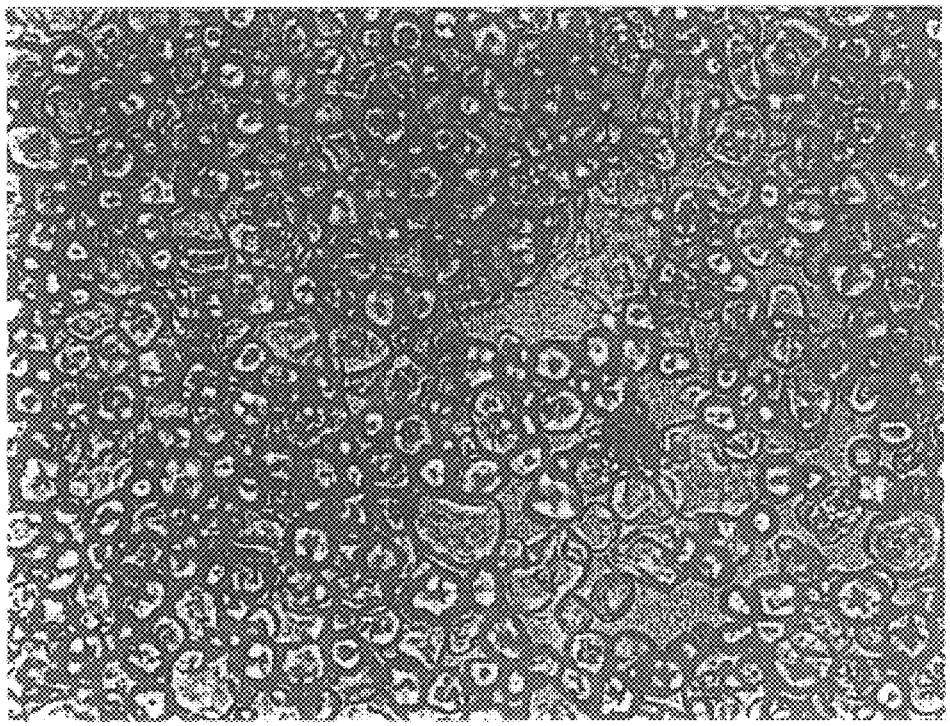
FIG. 1 shows a partially swollen white maize starch processed at 61° C. (by polarised optical microscopy). It shows the presence of a majority of non-swollen birefringent granules and a minority of swollen non-birefringent granules.
Figure 2:
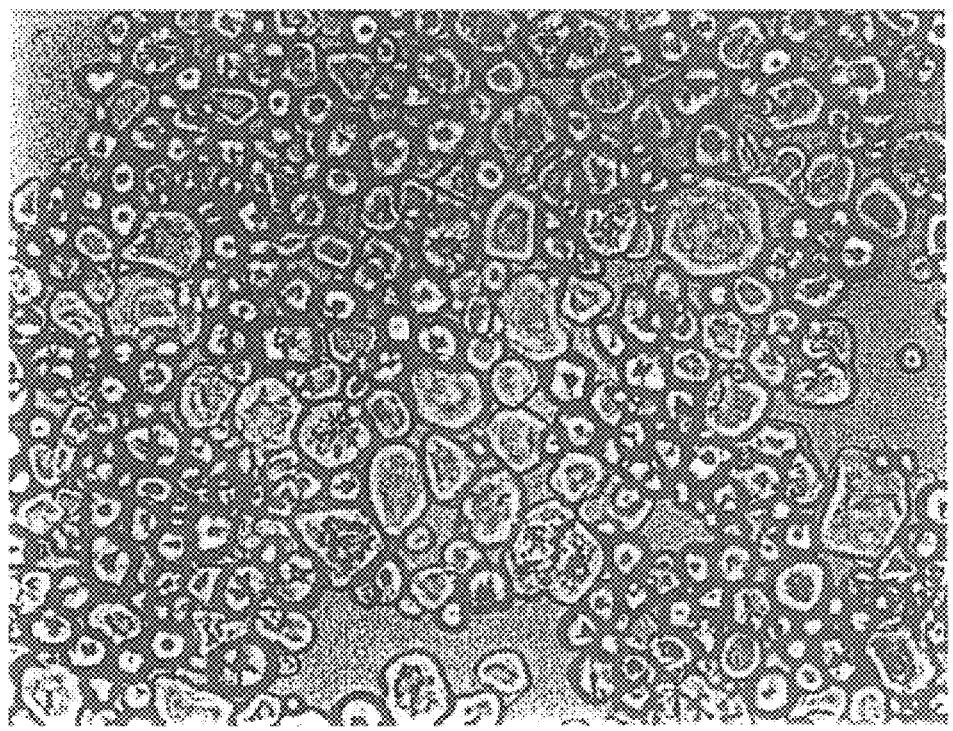
FIG. 2 shows a partially swollen white maize starch processed at 62° C. (by polarised optical microscopy). It shows the presence of more or less the same number of non-swollen birefringent granules and swollen non-birefringent granules.
Figure 3:
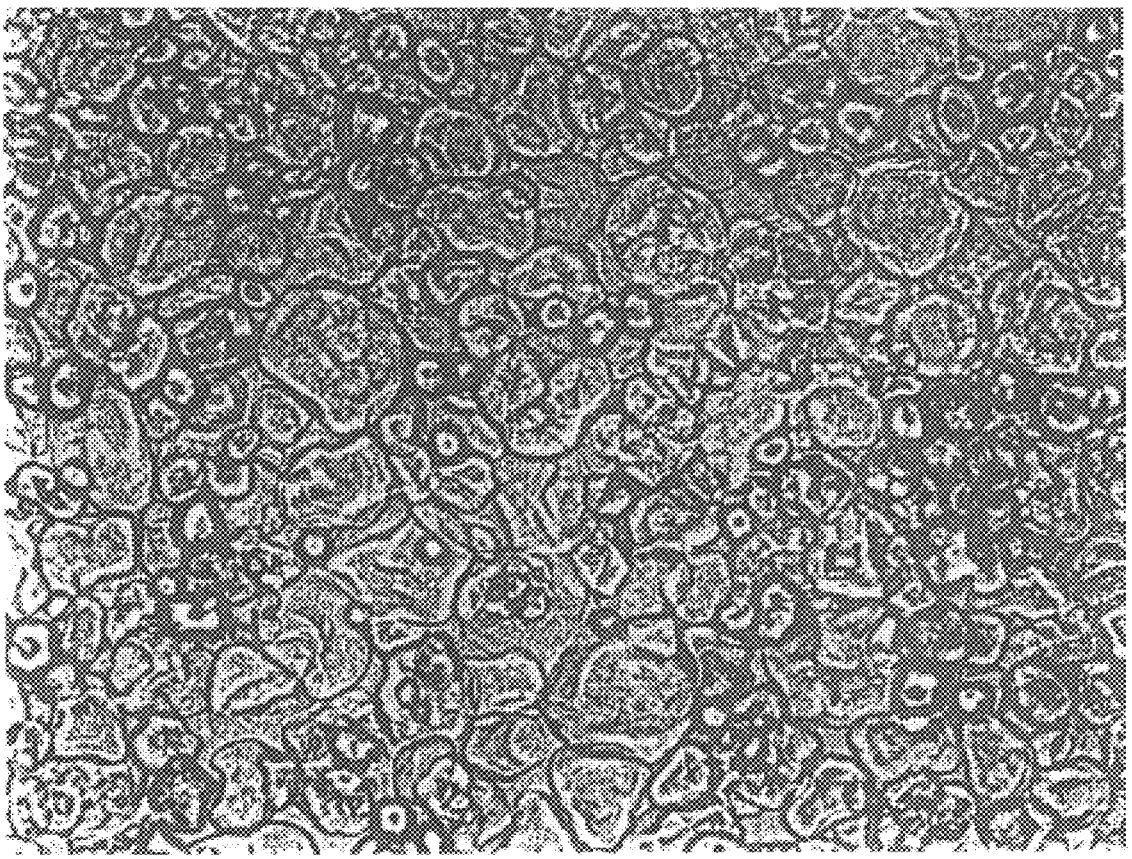
FIG. 3 shows a partially swollen white maize starch processed at 63° C. (by polarised optical microscopy). It shows the presence of a minority of non-swollen birefringent granules and a majority of swollen non-birefringent granules.
Figure 4:
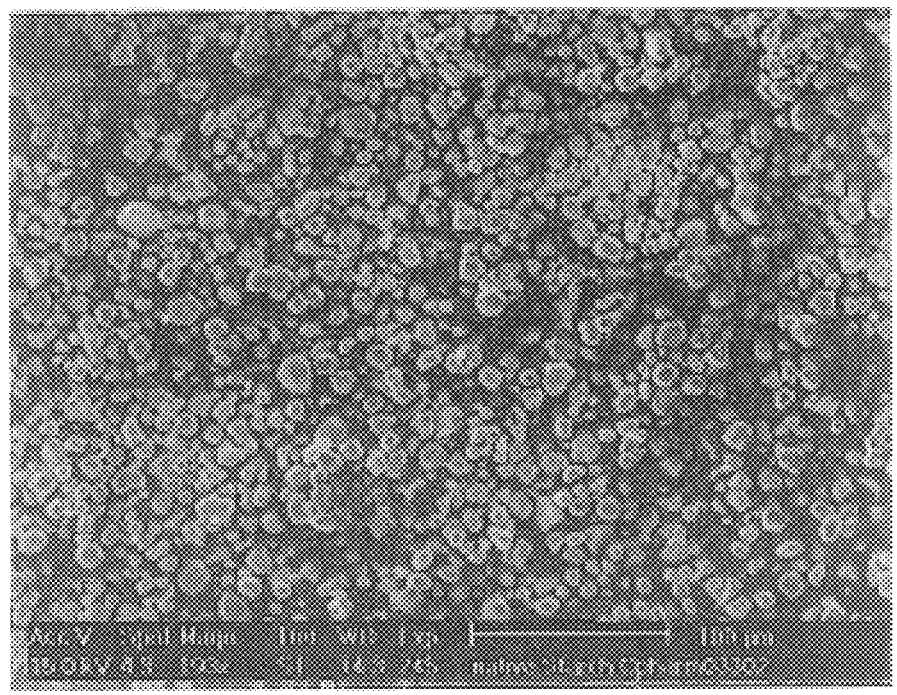
FIG. 4 shows native white maize starch granules by scanning electron microscopy.
Figure 5:
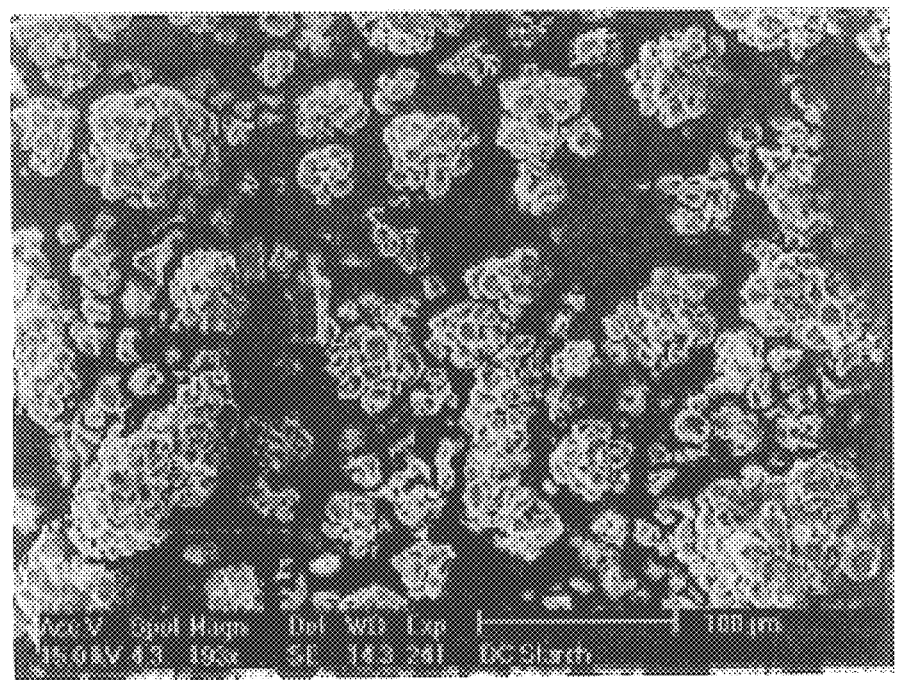
FIG. 5 shows a free-flowing directly compressible starch based on white maize granular starch according to the invention exemplified in Example 1 by scanning electron microscopy. Big and smooth granules can easily be identified.

As shown in Table 1, the above described free-flowing directly compressible starch is characterised by a particle size noticeably bigger than that of the raw material starch typically centred on 95 micrometers. As seen by polarised microscopy (see FIGS. 1 to 3), swelling of starch granules depends very much on the heating temperature of the slurry. A heating temperature of 61–62° C. produces granules with a typical ratio between non-swollen birefringent granules and swollen non-birefringent granules of around 50/50 (FIGS. 1 and 2). A heating temperature of 63° C. results in a product showing a much smaller proportion swollen non-birefringent granules (FIG. 3).

EXAMPLE 2

This example describes the production of a free-flowing directly compressible starch powder based on a granular high-amylose maize starch hybrid. The granular high-amylose maize starch powder was diluted in demineralised water in order to form a slurry at a concentration of 20% calculated on dry substance resulting in a slurry with a relative density of 1.050 compared to water. The starch slurry was then heated in a direct steam injection heat exchanger at a temperature of 95° C. with a variation of no more than ±1° C. The heating time was maintained for a time of 1 minute. The partially swollen starch slurry was then cooled down to a temperature of 50° C. by cold water. Drying of the cooled partially swollen starch slurry was carried out using a Niro FSD 4 spray-drying tower equipped with nozzles and fed at 10 liter/h. The inlet temperature was fixed at 200° C. and the outlet temperature was fixed at around 80° C. in order to obtain a product with a final dry substance of around 85%.

The free-flowing powder obtained as described showed an average particle size of 85 μm compared to 20 μm for the initial granular high-amylose maize as shown in Table 2.

amylose maize starch produced according to the process described in Example 2, are more than significantly higher than that of a standard compressible starch at any compression forces. This fact which directly results from the high binding capacity of the above mentioned starches allows the manufacture of tablets of similar hardness at lower compression forces resulting in significant advantages in the course of the tabletting process.

TABLE 2

| Starch | 1–10 μm | 10–25 μm | 25–50 μm | 50–75 μm | 75–100 μm | 100–125 μm | 125–150 μm | 150–200 μm | 200–300 μm | loose density |
|---|---|---|---|---|---|---|---|---|---|---|
| Native (%) | 12.5 | 80.1 | 6.5 | 0.7 | 0.2 | 0 | 0 | 0 | 0 | 500 g/l |
| Processed (%) | 0.9 | 6.9 | 18.1 | 20.6 | 25.2 | 10.9 | 7.4 | 6.3 | 3.7 | 300 g/l |

As shown in Table 2, the above described free-flowing direct compressible starch is characterised by a particle size noticeably bigger than that of the raw material starch typically centred on 85 micrometers.

EXAMPLE 3

This example demonstrates the advantages of directly compressible free-flowing starches obtained as described in Example 1 and Example 2 compared to conventional compressible starches when used for the production of tablets by direct compression. Tablets were formulated with 98.8% starch, 1% magnesium stearate Ph.Eur.III (Tramedico) and 0.2% silicon dioxide (Aerosil 200–Degussa). The starch was sieved over a 0.8 mm sieve and blended with silicon dioxide for 15 min. at 12 rpm. in a low-shear drum mixer. Magnesium stearate was added to the mix and blended for 3 min. at 12 rpm. All tabletting trials were performed on a triple punch rotary Korch tabletting press at a speed of 40 rpm to produce 1 cm$^2$ flat faced tablets of a weight of 350 mg. Hardness and dimensions of tablets were measured on a PharmaTest PTB-311 tablet-test unit. The disintegration time of tablets was determined on a PharmaTest PTZ-E in water at 37° C. The friability was measured on a PharmaTest PTF-E friabilator. The results are summarised as shown in Tables 3 to 5.

TABLE 3

| Compression | Tensile strength (N/mm$^2$) | | | | | |
|---|---|---|---|---|---|---|
| force (kN) | 5 | 10 | 15 | 20 | 25 | 30 |
| Processed white maize * | 0.4 | 1.6 | 2.6 | 3.2 | 3.5 | 3.6 |
| Processed high-amylose ** | 1.7 | 4.1 | 5.6 | 6.5 | 6.8 | 7 |
| Starch 1500 ™ (Colorcon) *** | 0.2 | 0.5 | 1 | 1.3 | 1.5 | 1.6 |

\* Free-flowing white maize starch produced as described in Example 1
\*\* Free-flowing high-amylose maize starch produced as described in Example 2
\*\*\* Starch 1500 ™ standard moisture from Colorcon Company Table 3 shows clearly that the hardness, directly indicated by tensile strength measurements, of tablets obtained by direct compression of the free-flowing white maize starch produced according to the process described in Example 1 and, to an even bigger extent, the hardness of tablets obtained by direct compression of the free-flowing high-

TABLE 4

| Compression | Disintegration time (min.) | | | | | |
|---|---|---|---|---|---|---|
| force (kN) | 5 | 10 | 15 | 20 | 25 | 30 |
| Processed white maize * | 1.8 | 3.8 | 5.9 | 6.6 | 7.1 | 7.1 |
| Processed high-amylose ** | 1.5 | 3.5 | 5 | 6 | 6.5 | 7 |
| Starch 1500 ™ (Colorcon) *** | 10.7 | 15 | 25 | 30 | no disint | no disint |

\* Free-flowing white maize starch produced as described in Example 1
\*\* Free-flowing high-amylose maize starch produced as described in Example 2
\*\*\* Starch 1500 ™ standard moisture from Colorcon Company Table 4 shows clearly that the disintegration times of tablets obtained by direct compression of the free-flowing white maize starch produced according to the process described in Example 1 and of tablets obtained by direct compression of the free-flowing high-amylose maize starch produced according to the process described in Example 2, are in the range of being five times smaller than that of a standard compressible starch at any compression forces. This results in significant advantages for the delivery of the active ingredients formulated with the above mentioned starches.

TABLE 5

| Compression | Friability (%) | | | | | |
|---|---|---|---|---|---|---|
| force (kN) | 5 | 10 | 15 | 20 | 25 | 30 |
| Processed white maize * | 2.5 | 0.3 | 0.2 | 0.1 | 0.1 | 0.1 |
| Processed high-amylose ** | 0.3 | 0.1 | <0.1 | <0.1 | <0.1 | <0.1 |
| Starch 1500 ™ (Colorcon) *** | 4.5 | 3.2 | 1.2 | 0.8 | 0.7 | — |

\* Free-flowing white maize starch produced as described in Example 1
\*\* Free-flowing high-amylose maize starch produced as described in Example 2
\*\*\* Starch 1500 ™ standard moisture from Colorcon Company Table 5 shows that even though they have much better disintegration times, at any compression force, the tablets obtained by direct compression of the free-flowing white maize starch produced according to the process described in Example 1 and the tablets obtained by direct compression of the free-flowing high-amylose maize starch produced according to the process described in Example 2, have friability patterns significantly lower than that of the standard compressible starch. Therefore, handling and processing of tablets obtained using above mentioned starches are easier and safer.

As a conclusion it can be stated that tablets obtained using free-flowing directly compressible starches produced according to Examples 1 and 2 as binders and disintegrants are characterised by high hardness at relatively low compression forces whilst they are also capable of disintegrating in an aqueous medium at a very high speed, and additionally exhibit a low friability pattern.

EXAMPLE 4

This example demonstrates the advantage of directly compressible free-flowing white maize starch powder obtained as described in Example 1 compared to a conventional compressible starch when used for the production of aspirin tablets by direct compression. Tablets were formulated with 18.8% starch, 80% aspirin, 0.5% magnesium stearate Ph.Eur.III (Tramedico) and 0.2% silicon dioxide (Aerosil 200–Degussa). The starch and aspirin were sieved over a 0.8 mm sieve and blended together with the silicon dioxide and the magnesium stearate for 15 min. at 12 rpm. in a low-shear drum mixer. All tabletting trials were performed on a triple punch rotary Korsh tabletting press at a speed of 40 rpm to produce 1 cm² tablets of a weight of 450 mg. Hardness and dimensions of tablets were measured on a PharmaTest PTB-311 tablet-test instrument. The disintegration time of tablets was determined on a PharmaTest PTZ-E in water at 37° C. The friability of the tablets was measured on a PharmaTest PTF-E friabilator. The results are summarised as shown in Table 6.

TABLE 6

| Compression force (kN) | 15 | 20 | 25 | 30 |
|---|---|---|---|---|
| Tensile strength (N/mm²) | | | | |
| Aspirin + Processed white maize * | 1.25 | 1.5 | 1.6 | 1.65 |
| Aspirin + Starch 1500 ™ (Colorcon) * * | 0.7 | 0.8 | 0.9 | 0.95 |
| Disintegration time (min.) | | | | |
| Aspirin + Processed white maize * | 1.25 | 2 | 2.9 | 3 |
| Aspirin + Starch 1500 ™ (Colorcon) * * | 7 | 10 | 11 | 12.5 |
| Friability (%) | | | | |
| Aspirin + Processed white maize * | 0.8 | 0.62 | 0.55 | 0.52 |
| Aspirin + Starch 1500 ™ (Colorcon) * * | 1.75 | 1.4 | 1.2 | 1.25 |

\* Free-flowing white maize starch produced as described in Example 1
\* \* Starch 1500 ™ standard moisture from Colorcon Company Table 6 shows clearly that the hardness, directly indicated by tensile strength, of tablets obtained by direct compression of aspirin plus the free-flowing white maize starch produced according to the process described in Example 1 as binder-disintegrant is significantly higher than that of a standard compressible starch at any compression force. This fact which directly results from the high binding capacity of the above mentioned starches allows the manufacture of tablets of similar hardness at lower compression forces resulting in significant advantage in the course of the tabletting process. It also demonstrates clearly that the disintegration times are in the range of being four to five times smaller resulting in significant advantages for the delivery of aspirin so formulated. Another advantage of formulating aspirin with the free-flowing white maize starch produced according to the process described in Example 1 as binder-disintegrant resumes in a significantly lower friability resulting in easier and safer handling and processing of tablet.

As a conclusion it can be stated that formulating active ingredients such as aspirin in tablets by direct compression using free-flowing directly compressible starch produced according to Example 1 as binder-disintegrant results in tablets of higher hardness, lower disintegration times and lower friability profiles at relatively lower compression forces.

What is claimed is:

1. A free-flowing directly compressible processed starch powder in that comprises regular and smooth partially swollen granules of starch, wherein the ratio of non-swollen birefringent granules to swollen non-birefringent granules is in the range of from 1:5 to 5:1 and has an average particle size greater than 50 μm and a moisture content of from 3 to 15% by weight, wherein when said free-flowing compressible processed starch powder is compressed into a tablet under a compression force of 10 kN gives a tablet having a tensile strength of at least 1 N/mm².

2. A free-flowing compressible processed starch powder according to claim 1, wherein the ratio of non-swollen birefringent granules to partially swollen non-birefringent granules is in the range of from 1:2 to 2:1.

3. A free-flowing compressible processed starch powder according to claim 2, wherein the ratio of non-swollen birefringent granules to partially swollen non-birefringent granules is about 1:1.

4. A free-flowing compressible processed starch powder according to any one of claims 1 to 3, wherein at least 50% of the particles have a particle size of 75 μm or greater.

5. A free-flowing compressible processed starch powder according to any one of claims 1 to 3, which when compressed into a tablet under a compression force of 10 kN to 30 kN gives a tablet having a tensile strength of at least 1 N/mm².

6. A process for preparing a free-flowing compressible starch powder comprising the steps; 1) preparing a slurry of starch in water, 2) heating the slurry to a temperature not substantially higher than the gelatinisation temperature of the starch to cause partial swelling of the starch granules without causing disruption of the starch granules, 3) cooling the starch slurry to prevent any further swelling of the starch granules and 4) spray-drying the cooled slurry to produce a free-flowing starch powder having a moisture content of from 3 to 15% by weight.

7. A process according to claim 6, wherein the slurry is heated to a temperature which is +/−5° C. of the gelatinisation temperature of the starch.

8. A process according to either claim 6 or claim 7, wherein the starch slurry after the heating step is cooled to a temperature which is 5° to 15° C. lower than the temperature used in the heating step.

9. A composition for forming a tablet comprising at least one active material and, as binder or filler, a free-flowing directly compressible processed starch powder according to any one of claims 1 to 3.

10. A dry compressed tablet comprising at least one active material and, as binder or filler, processed starch, said processed starch comprising regular and smooth partially swollen granules of starch wherein the ratio of non-swollen birefringent granules to swollen birefringent granules is in the range of from 1:5 to 5:1 and having an average particle size greater than 50 μm and a moisture content in the range of from 3 to 15% by weight, said tablet, when formed under a compression force of 15 kN having a tensile strength greater than 1 N/mm², a disintegration time in water at 37° C. of less than 6 minutes and % friability of less than 1%.

11. A process according to claim 6, wherein the slurry is heated to a temperature which is ±3° C. of the gelatinisation temperature of the starch.

12. A process according to claim 6, wherein the slurry is heated to a temperature which is ±1° C. of the gelatinisation temperature of the starch.

13. A process according to either claims 11 or 12, wherein after the heating step the starch slurry is cooled to a temperature which is 5° C. to 15° C. lower than the temperature used in the heating step.

14. A process for producing a dry compressed tablet from a free-flowing directly compressible process starch powder, said free-flowing directly compressible starch powder comprising regular and smooth partially swollen granules of starch wherein the ratio of non-swollen birefringement granulers to swollen non-birefringement granules is in the range of 1:5 to 5:1 and as having an average particle size greater than 50 μm and a moisture content of from 3 to 15% by weight, said process comprising directly compressing the starch powder under a low compression force of at least 10 kN to obtain a tablet having a tensile strength of at least 1 N/mm².

15. A process for preparing a tablet according to claim 14, wherein the free-flowing directly compressible process starch powder has an average particle size value of 50 μm to 500 μm.

16. A process for preparing a tablet according to claim 15, wherein the free-flowing directly compressible starch powder has a moisture content of 5–10%.

17. A process according to claim 15, wherein the compression force is up to 30 kN.

18. A process according to claim 15, wherein the free-flowing directly compressible starch powder has an average particle size of from 50 μm to 500 μm.

19. A free-flowing compressible process starch powder according to claim 4, which when compressed into a tablet under a compression of 10 kN to 30 kN is a tablet having a tensile strength of at least 1 N/mm².

* * * * *